United States Patent [19]

Weisse et al.

[11] Patent Number: 5,329,050
[45] Date of Patent: Jul. 12, 1994

[54] PROCESS FOR THE PREPARATION OF SUBSTITUTED INDANONES, AND THEIR USE

[75] Inventors: Laurent Weisse, Oberursel; Jürgen Rohrmann, Kelkheim; Frank Küber, Oberursel; Heinz Strutz, Usingen, all of Fed. Rep. of Germany

[73] Assignee: Hoechst Aktiengesellschaft, Frankfurt am Main, Fed. Rep. of Germany

[21] Appl. No.: 53,835

[22] Filed: Apr. 27, 1993

[30] Foreign Application Priority Data

Apr. 28, 1992 [DE] Fed. Rep. of Germany ....... 4213940

[51] Int. Cl.$^5$ ............................................. C07C 45/45
[52] U.S. Cl. .................... 568/319; 568/323; 568/326; 568/327
[58] Field of Search ................. 512/15; 508/319, 323, 508/326, 327

[56] References Cited

U.S. PATENT DOCUMENTS

| | | | |
|---|---|---|---|
| 1,754,031 | 4/1930 | Mayer et al. | 568/319 |
| 2,456,452 | 12/1948 | Seeger | 568/323 |
| 3,324,174 | 6/1967 | Braun et al. | 568/319 |
| 3,466,333 | 9/1969 | Bruson et al. | 512/15 |
| 3,769,348 | 10/1973 | Wood et al. | 512/15 |
| 4,132,737 | 1/1979 | Molloy | 568/319 |
| 4,322,414 | 3/1982 | Hokama et al. | 424/214 |
| 4,541,948 | 9/1985 | Joulain | 512/15 |
| 4,670,603 | 6/1987 | Piccolo et al. | 568/319 |

FOREIGN PATENT DOCUMENTS 0203276 12/1986 European Pat. Off. .
3519009 11/1986 Fed. Rep. of Germany .

OTHER PUBLICATIONS

Marquardt, Helv. Chim Acta., vol. 48, pp. 1476–1485 (1965).
Hurt et al, J.A.C.S., vol. 72, pp. 3286–3287 (1950).
Journal of the American Chemical Society, vol. 61, 1939, pp. 1272–1281.

*Primary Examiner*—James H. Reamer

[57] ABSTRACT

1-Indanones of the formula IV or IVa

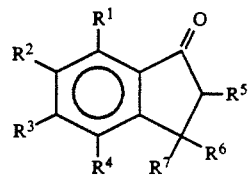

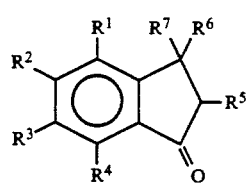

in which $R^1$ and $R^7$ are preferably hydrogen or alkyl, or adjacent radicals $R^1$ to $R^4$ form a ring, are obtained in a one-step reaction by reacting a compound I

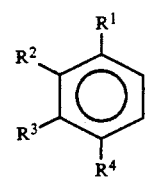

with a compound of the formula II or a compound III

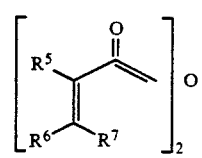

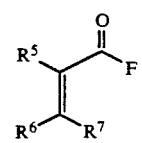

in liquid hydrogen fluoride.

6 Claims, No Drawings

PROCESS FOR THE PREPARATION OF SUBSTITUTED INDANONES, AND THEIR USE

The present invention relates to a technically simple process for the preparation of substituted 1-indanones.

Compounds of this type are important intermediates in the preparation of metallocene complexes, since 1-indanones can readily be converted into the corresponding indenes. Indenes are used as a ligand system for the synthesis of metallocene complexes (EP-A 366 128). In particular the corresponding bridged, chiral zirconium derivatives are of considerable importance as highly active catalysts in the polymerization of olefins (cf. EP-A 129 368 and EP-A 321 852). By varying the ligand system, for example by substitution, the catalyst properties can be modified in a targeted manner. This makes it possible to change the polymer yields, the molecular weight, the tacticity or the melting point of the polymers in the desired extent (New J. Chem. 14 (1990) 499; Organomet. 9 (1990) 3098; Angew. Chem. 102 (1990) 339; EP-A 316 155; EP-A 351 392).

Furthermore, substituted 1-indanones are of industrial importance as fragrances (EP-A 162 465) and as valuable intermediates in the preparation of pharmaceutical products or other bioactive compounds (EP-A 421 759; J. Med. Chem. 25 ( 1990 ) 765 ).

The literature describes a number of processes for the preparation of substituted 1-indanones.

1-Indanones which carry substituents on the 6-membered ring can be prepared starting from the correspondingly substituted aromatic compounds by fusing on the 5-membered ring in 2- to 6-step syntheses (J. Org. Chem., 55 (1990) 247; Bull. Soc. Chim. Fr. 6 (1969) 1981).

Processes for the preparation of 1-indanones which carry substituents on the 5-membered ring or on both rings are likewise known (J. Org. Chem. 46 (1981) 3758; J. Org. Chem. 23 (1958) 1441 ).

These methods have the disadvantage that they are generally multistep and give only poor overall yields of the desired products. Many of the syntheses are not universally applicable, but are restricted to specific derivatives. In others, the starting materials are poorly accessible or very expensive. Certain substitution patterns on the aromatic rings can likewise not be achieved by these methods. The few known one-step syntheses have the disadvantage that they are restricted to specific derivatives and give poor yields, so that technically complex purification operations of the products are necessary. Most of these reactions are carried out with the aid of Friedel-Crafts catalysts, such as, for example, AlCl$_3$, which are employed in excess. These reactions require technically complex work-up steps, which are associated with production of a large amount of salt. Also known are processes for the preparation of substituted indanones by reacting aromatic compounds, such as xylene or acenaphthene, with aqueous methacrylic acid, crotonic acid or cinnamic acid in a large excess of liquid hydrogen fluoride (J. Am. Chem. Soc. 61 (1939) 1272; J. Am. Chem. Soc. 72 (1950) 3287). The yields are between 62% and 81%. This method has the disadvantage that water present or formed causes considerable corrosion problems. Recycling of the hydrogen fluoride is likewise not possible due to the presence of water. The hydrofluoric acid must be neutralized, producing a large amount of salt which is difficult to dispose of. In addition, the products must also be purified due to the low yields.

The object was thus to find a process for the preparation of the abovementioned indanones which avoids the disadvantages known from the prior art.

It has been found that aromatic compounds of the formula I below react virtually quantitatively with commercial carboxylic anhydrides of the formula II or carboxylic acid fluorides of the formula III in liquid hydrogen fluoride to give indanones of the formula IV/IVa.

The present invention therefore relates to a process for the preparation of a compound of the formula IV or the isomer thereof of the formula IVa

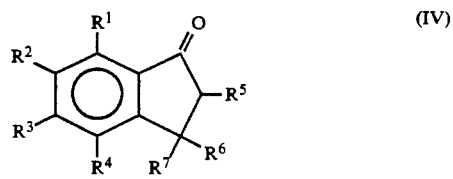

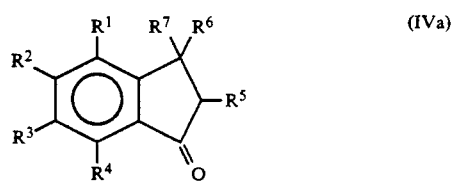

in which $R^1$, $R^2$, $R^3$, $R^4$, $R^5$, $R^6$ and $R^7$ are identical or different and are hydrogen, (C$_1$-C$_{20}$)-alkyl, (C$_6$-C$_{14}$)aryl, (C$_1$-C$_{10}$)alkoxy, (C$_2$-C$_{10}$)alkenyl, (C$_7$-C$_{20}$)arylalkyl, (C$_7$-C$_{20}$)alkylaryl, (C$_6$-C$_{10}$)aryloxy, (C$_1$-C$_{10}$)-fluoroalkyl, (C$_6$-C$_{10}$)haloaryl, (C$_2$-C$_{10}$)alkynyl, an —SiR$^8_3$ radical in which R$^8$ is (C$_1$-C$_{10}$)alkyl, or are a halogen atom or a heteroaromatic radical having 5 or 6 ring members which may contain one or more heteroatoms, or the adjacent radicals R$^1$-R$^4$, together with the atoms connecting them, form one or more substituted or unsubstituted rings, which comprises reacting a compound of the formula I

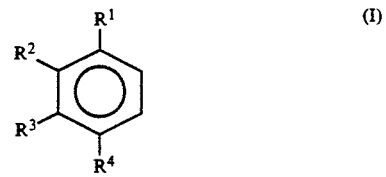

with a compound of the formula II

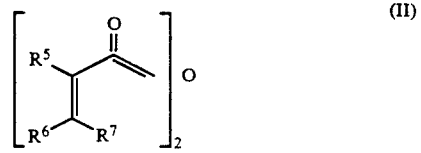

or with a compound of the formula (III)

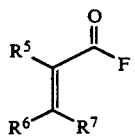
(III)

in which $R^1-R^7$ are as defined above, in liquid, anhydrous hydrogen fluoride.

Alkyl here is straight-chain or branched alkyl. Halogen is fluorine, chlorine, bromine or iodine, in particular fluorine or chlorine. Examples of heteroaromatic radicals are thienyl, furyl or pyridyl.

The rings formed by adjacent radicals $R^1-R^4$ may be substituted by substituents as defined for $R^1-R^7$, including the preferred meanings mentioned therefor.

In the formulae IV and IVa, $R^1$, $R^2$, $R^3$ and $R^4$ are preferably identical or different and are hydrogen, $(C_1-C_{10})$alkyl, $(C_6-C_{14})$aryl, $(C_1-C_4)$alkoxy, $(C_2-C_6)$alkenyl, $(C_1-C_6)$fluoroalkyl or a halogen atom, or the radicals $R^1$ and $R^2$, $R^2$ and $R^3$ or $R^3$ and $R^4$, together with the atoms connecting them, form a substituted or unsubstituted five- or six-membered ring, $R^5$ is $(C_1C_{10})$alkyl and $R^6$ and $R^7$ are hydrogen.

In particular, $R^1$, $R^2$, $R^3$ and $R^4$ are identical or different and are hydrogen or $(C_1-C_{10})$alkyl, or the radicals $R^1$ and $R^2$, $R^2$ and $R^3$ or $R^3$ and $R^4$, together with the atoms connecting them, form a substituted or unsubstituted, six-membered, saturated or unsaturated carbocyclic ring, $R^5$ is methyl, and $R^6$ and $R^7$ are hydrogen.

The saturated or unsaturated five- or six-membered ring (carbocyclic ring) formed by adjacent substituents $R^1-R^4$ may carry additional substituents, preferably $(C_1-C_{10})$ alkyl.

Depending on the substitution pattern on the aromatic ring, the indanones may be formed in the form of two constitutional isomers of the formulae IV and IVa. Depending on the application, these may be further reacted in pure form or as a mixture. In the preparation of metallocene complexes, the isomer mixture can be employed.

The indanones IV/IVa are preferably prepared by reacting aromatic compounds of the formula I with anhydrides of the formula II.

The starting compounds of the formula I are known and are commercially available. The starting compounds of the formula II are commercially available or can be prepared by methods known from the literature (cf., for example, Advanced Organic Chemistry, 1983, 369).

The carboxylic acid fluorides of the formula III can be prepared from known carboxylic acid chlorides or carboxylic anhydrides (formula II) by reaction with HF in the manner known from the literature (cf., for example, Advanced Organic Chemistry, 1983, 399).

In the preparation of the compounds IV/IVa, additional solvent can be added to the hydrogen fluoride, but the reaction is preferably carried out in pure, anhydrous hydrogen fluoride.

The molar ratios between the starting compounds, including the hydrogen fluoride, can vary within broad limits. The molar ratio of compound I:II (or III): HF is preferably 1:0.5–2.0:5–100, in particular 1:0.9–1.2:20–50, i.e. the reaction is carried out in an excess of hydrogen fluoride.

The reaction temperature is preferably from $-30°$ C. to $130°$ C., in particular from $0°$ C. to $80°$ C.

The reaction times generally vary between 30 minutes and 50 hours, preferably between 1 hour and 24 hours.

The reaction is preferably carried out in a pressure range of 1–15 atm.

It is preferred to initially introduce a mixture of the compounds I and II (or III) and to meter in the hydrogen fluoride. The reverse sequence of addition is also possible.

When the reaction is complete, the hydrogen fluoride can be removed by distillation and recovered virtually quantitatively without significant impurities.

The indanones of the formulae IV and IVa can be freed from acid components by washing with $Na_2CO_3$, $NaHCO_3$ or KOH solution and water and dried using conventional dessicants, such as $Na_2SO_4$, $MgSO_4$ or molecular sieves. Since the reactions are generally virtually quantitative, further purification is in most cases unnecessary. However, filtration through silica gel, aluminum oxide or filtration aids, such as, for example, Celite, is frequently advisable. If necessary, the further purification can be carried out by distillation, column chromatography or crystallization. If necessary, the constitutional isomers IV and IVa can be separated from one another by column chromatography on silica gel or aluminum oxide.

The process according to the invention is distinguished, in particular, by the fact that variously substituted 1-indanones can be obtained very selectively and in virtually quantitative yield in a simple and short synthesis (one-step process). Complex purification of the derivatives is therefore unnecessary, in contrast to the prior art. A further advantage is that the hydrogen fluoride used as catalyst can be recovered virtually quantitatively and re-used, since no water is formed during the reaction. This has the further, industrially crucial advantage that corrosion problems caused by aqueous hydrofluoric acid are avoided. This method thus represents an economically and ecologically very favorable process for the preparation of substituted 1-indanones. The substitution pattern on the five- and six-membered rings can be varied in a very broad range, also allowing access to novel 1-indanone derivatives.

The indanones IV/IVa are preferably used for the preparation of metallocenes used as highly active catalyst components in the polymerization of olefins (cf., for example, EP-A 336 128). To this end, the indanones, preferably as an isomer mixture, are first reduced to the corresponding indanols by methods known from the literature using reducing agents such as $NaBH_4$ or $LiAlH_4$, and these are subsequently dehydrated to give the corresponding indenes using acids such as sulfuric acid, oxalic acid or p-toluenesulfonic acid or alternatively by treatment with dehydrating substances such as magnesium sulfate, sodium sulfate, aluminum oxide, silica gel or molecular sieves (Bull. Soc. Chim. Fr. 11 (1973) 3092; Organomet. 9 (1990) 3098).

The substituted indenes may be obtained as double-bond isomers. These can be purified from byproducts by distillation, column chromatography or crystallization. Isomers can be employed, as a mixture, directly for the synthesis of the corresponding metallocene complexes.

The synthesis of the metallocenes starting from indenes is known (AU-A-31478/89; J. Organomet. Chem. 342 (1988) 21; EP-A 284 707).

The examples below serve to illustrate the invention in greater detail.

EXAMPLE A

6,7-Benzo-2-methylindan-1-one (1) and 4,5-benzo-2-methylindan-1-one (1a)

100 g (5 mol) of anhydrous HF were added to 12.6 g (98 mmol) of naphthalene and 15.8 g (103 mmol) of methacrylic anhydride in a 250 ml stainless-steel autoclave, and the mixture was stirred at 50° C. for 18 hours. The hydrogen fluoride was subsequently removed by distillation, and the residue was taken up in ethyl acetate and neutralized using dilute KOH solution. The aqueous phase was separated off and extracted twice with ethyl acetate. The combined organic phases were dried using $MgSO_4$ and freed from solvent under reduced pressure, giving 19.0 g (99% of theory) of a pale brown oil. The selectivities to 1 and 1a were 58% and 39% respectively.

$^1H$—NMR spectra (100 MHz, $CDCl_3$): 1: 9.15 (m, 1H), 7.40–8.10 (m,5H), 3.47 (dd, 1H), 2.62–2.95 (m,2H), 1.37 (d,3H); 1a: 7.4–8.0 (m,6H), 3.70 (dd,1H), 2.75–3.10 (m,2H), 1.40 (d,3H).

Mass spectrum: 196 M+, correct decomposition pattern.

EXAMPLE B

6,7-Benzo-2-methylindan-1-one (1) and 4,5-benzo-2-methylindan-1-one (1a)

120 g (0.94 mol) of naphthalene and 153 ml (1.03 mol) of methacrylic anhydride were introduced into a 2 l stainless-steel autoclave, and 1000 g of HF were slowly added at room temperature. The mixture was slowly warmed to 60° C. and kept at this temperature for 18 hours. The hydrogen fluoride was subsequently condensed off at 30°–35° C. and recovered. The residue was taken up in ethyl acetate and washed twice with water, twice with saturated $NaHCO_3$ solution and once with NaCl solution. Filtration through silica gel and removal of the solvent under reduced pressure gave 180 g (98% of theory) of the pure isomer mixture 1/1a. The selectivities to 1 and 1a were 60% and 40% respectively.

EXAMPLE C

5,7-Diisopropyl-2-methylindan-1-one (2) and 4,6-diisopropyl-2-methylindan-1-one (2a)

15.6 g (96 mmol) of 1,3-diisopropylbenzene and 15.8 g (103 mmol) of methacrylic anhydride were reacted with HF analogously to Example A and worked up, giving 22 g (99% of theory) of a pale brown oil. The selectivities to 2 and 2a were 66% and 30% respectively.

$^1H$—NMR spectrum (360 MHz, $CDCl_3$): isomer mixture 7.49 (d), 7.36 (d), 7.13 (s), 7.10 (s), 4.15 (sept.), 3.25–3.40 (m), 3.10 (sept), 2.90–3.00 (m), 2.60–2.73 (m), 1.22–1.30 (m). Mass spectrum: 230 M+, correct decomposition pattern.

EXAMPLE D

5,7-Diisopropyl-2-methylindan-1-one (2) and 4,6-diisopropyl-2-methylindan-1-one (2a)

15.6 g (96 mmol) of 1,3-diisopropylbenzene and 15.8 g (103 mmol) of methacrylic anhydride were reacted and worked up analogously to Example C. The crude mixture was chromatographed on 700 g of silica gel 60. Using an eluent mixture of hexane/ethyl acetate (20:1) whose composition was changed during the chromatography to a ratio of 10:1, first 14.0 g (63% of theory) of the indanone 2 and subsequently 6.2 g (28% of theory) of the indanone 2a were eluted. The compounds were obtained in the form of colorless to yellowish oils.

$^1$H-NMR spectrum 2 (360 MHz, $CDCl_3$): 7.13 (s,1H), 7.10 (s,1H), 4.15 (sept.,1H), 3.30 (m, 1H), 2.95 (sept.,1H); 2.65 (m,2H), 1.23–1.32 (m,15H).

$^1$H-NMR spectrum 2a (360 MHz, $CDCl_3$): 7.49 (d,1H), 7.36 (d,1H), 3.35 (m, 1H), 3.09 (sept.,1H), 2.95 (sept.,1H); 2.70 (m,2H), 1.24–1.33 (m,15H).

EXAMPLE E

2,5-Dimethylindan-1-one (3) and 2,6-dimethylindan-1-one (3a)

100 g (5 mol) of HF were added to 9.21 g (100 mmol) of toluene and 15.4 g (100 mmol) of methacrylic anhydride in a 250 ml stainless-steel autoclave, and the mixture was stirred at 50° C. for 4 hours. The work-up was carried out analogously to Example A, giving 15.2 g (95%) of the product mixture as a pale brown oil. The selectivities to 3 and 3a were 85% and 6% respectively.

$^1H$—NMR spectrum (100 MHz, DMSO): 7.14–7.59 (m), 3.15–3.50 (m), 2.45–2.80 (m), 2.4 (s), 1.12–1.27 (d). Mass spectrum: 160 M+, correct decomposition pattern.

EXAMPLE F

5-Isobutyl-2-methylindan-1-one (4)

100 g (5 mol) of HF were added to 13.4 g (100 mmol) of isobutylbenzene and 15.4 g (100 mmol) of methacrylic anhydride in a 250 ml stainless-steel autoclave, and the mixture was stirred at 50° C. for 5 hours. The work-up was carried out analogously to Example A, giving 19.4 g (96%) of the product 4 as a brownish oil. Filtration through silica gel with ethyl acetate gave 18.5 g (92%) of the pure indanone 4 as a yellowish oil.

$^1$H-NMR spectrum (100 MHz, $CDCl_3$): 7.7 (m), 7.2 (m), 3.35 (q), 2.70 (m), 2.58 (d), 1.95 (q), 1.25 (d), 0.93 (d). Mass spectrum: 202 M+, correct decomposition pattern.

EXAMPLE G

2,5,7-Trimethyl-1-indanone (5) and 2,4,6-trimethyl-1-indanone (5a)

10.6 g (100 mmol) of m-xylene (99%) and 15.4 g (100 mmol) of methacrylic anhydride were reacted with HF for 8 hours at room temperature analogously to Example A and worked up, giving 18 g ($\approx$100%) of the product 5+5a as a brown oil. Distillation of the crude product at 80°–84° C./0.1 mbar gave 16.0 g (92%) of the isomer mixture 5 and 5a as a colorless to slightly yellowish oil. The molar ratio between 5 and 5a is 1:1.

Mass spectrum: 174 M+, correct decomposition pattern. $^1H$—NMR spectrum (300 MHz, $CDCl_3$): 7.38 (s,1H), 7.22 (s,1H), 7.07 (s,1H), 6.89 (s,1H), 3.18–3.32 (m,2H), 2.46–2.74 (m,7H), 2.35–2.38 (2s,6H), 2.29 (s,3H), 1.30 (d,3H), 1.26 (d,3H).

EXAMPLE H

2-Methylindan-1-one (6)

7.8 g (100 mmol) of benzene and 15.4 g (100 mmol) of methacrylic anhydride were reacted with HF for 4 hours at room temperature analogously to Example A and worked up, giving 13.7 g (94%) of the product 6 as a brown oil. The crude product was chromatographed on 200 g of silica gel 60. Using an eluent mixture of hexane/methylene chloride 1:1, 12.2 g (84%) of the indanone 6 were obtained as a colorless oil.

¹H—NMR spectrum (100 MHz, CDCl₃): 7.5 (m), 3.33 (q), 2.73 (m), 1.30 (d).

Mass spectrum: 146 M+, correct decomposition pattern.

EXAMPLE J

2,4,5,6-Tetramethylindan-1-one (7)

12 g (100 mmol) of 1,2,3-trimethylbenzene and 15.4 g (100 mmol) of methacrylic anhydride were reacted with HF for 6 hours at room temperature analogously to Example A and worked up, giving 18.0 g (96%) of the indanone 7 as a brown oil. Distillation of the crude product at 0.05 mmHg/98°–104° C. gave 17.4 g (93%) of the pure compound 7 as a colorless oil.

¹H-NMR spectrum (100 MHz, CDCl₃): 7.2 (s,1H), 3.20 (m,14), 2.4–2.8 (m, 11H), 1.25 (d).

Mass spectrum: 188 M+, correct decomposition pattern.

EXAMPLE K

5-Phenyl-2-methylindan-1-one (8)

15.4 g (100 mmol) of biphenyl and 16 g (104 mmol) of methacrylic anhydride were reacted with 100 g (5 mol) of HF at 70° C. for 60 hours analogously to Example A. Work-up carried out analogously to Example A gave 23 g of (8) in a purity of 90% (93% of theory).

EXAMPLE L

8-Methyl-4,5,7,8-tetrahydrocyclopenta[e]acenaphthen-9-one (9)

30.84 g (200 mmol) of acenaphthene and 35 g (228 mmol) of methacrylic anhydride were reacted with 50 g (2.5 mol) of HF for 20 hours at 70° C. analogously to Example A. Work-up carried out analogously to Example A gave 44 g of (9) isolated in a purity of 92% (90% of theory).

EXAMPLE M

2-Methyl-3,9-dihydro-2H-cyclopenta[b]fluoren-1-one (10) and
2-methyl-2,10-dihydro-1H-cyclopenta[a]fluoren-3-one (10a)

33.24 g (200 mmol) of fluorene and 35 g (228 mmol) of methacrylic anhydride were reacted with 50 g (2.5 mol) of HF for 25 hours at 70° C. analogously to Example A. Work-up carried out analogously to Example A isolated 46 g of (10) and (10a). The purity of (10) and (10a) was 94% (yield 91.5% of theory), with the molar ratio between (10) and (10a) being 2:1.

EXAMPLE N

16-Methyl-6,7,15,16-tetrahydrocyclopenta[a]phenanthren17-one (11) and
9-methyl-5,6,9,10-tetrahydrocyclopenta[b]phenanthren-8-one (11a)

18 g (100 mmol) of 9,10-dihydrophenanthrene and 16 g (104 mmol) of methacrylic anhydride were reacted with 90 g (4.5 mol) of HF for 3 hours at 70° C. analogously to Example A. Work-up carried out analogously to Example A isolated 24.7 g of (11) and (11a). The purity of 11 and 11a was 92% (yield 91% of theory), with the molar ratio between 11 and 11a being 6:4.

EXAMPLE O

5-Methoxy-2-methylindan-1-one (12)

10.8 g (100 mmol) of anisole and 16 g (104 mmol) of methacrylic anhydride were reacted with 100 g (5 mol) of HF for 3 hours at 70° C. analogously to Example A. Work-up carried out analogously to Example A gave 17 g of (12) in a purity of 68% (yield 65% of theory).

EXAMPLE P

5,6-Dimethoxy-2-methylindan-2-one (13)

13.82 g (100 mmol) of veratrole and 16 g (104 mmol) of methacrylic anhydride were reacted with 100 g (5 mol) of HF for 18 hours at 30° C. analogously to Example A. Work-up carried out analogously to Example A gave 20.3 g of (13) in a purity of 96% (yield 93.5% of theory).

We claim:

1. A process for the preparation of a compound of the formula IV or the isomer thereof of the formula IVa

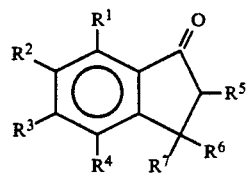

(IV)

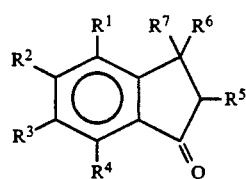

(IVa)

in which $R^1$, $R^2$, $R^3$, $R^4$, $R^5$, $R^6$ and $R^7$ are identical or different and are hydrogen, $(C_1-C_{20})$-alkyl, $(C_6-C_{14})$aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$-fluoroalkyl, $(C_6-C_{10})$ haloaryl, $(C_2-C_{10})$alkynyl, an —SIR$^8_3$ radical in which $R^8$ is $(C_1-C_{10})$alkyl, or are a halogen atom or a heteroaromatic radical having 5 or 6 ring members which may contain one or more heteroatoms, or the adjacent radicals $R^1$–$R^4$, together with the atoms connecting them, form one or more substituted or unsubstituted rings, which comprises reacting a compound of the formula I

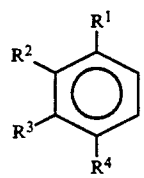

(I)

with a compound of the formula II

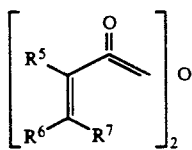

or with a compound of the formula (III)

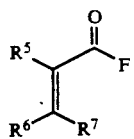

in which $R^1$–$R^7$ are as defined above, in liquid, anhydrous hydrogen fluoride.

2. The process as claimed in claim 1, wherein, in the formulae IV and IVa, $R^1$, $R^2$, $R^3$ and $R^4$ are identical or different and are hydrogen, $(C_1-C_{10})$alkyl, $(C_1-C_4)$alkoxy, $(C_2-C_6)$alkenyl, $(C_1-C_6)$fluoroalkyl or a halogen atom, or the radicals $R^1$ and $R^2$, $R^2$ and $R^3$ or $R^3$ and $R^4$, together with the atoms connecting them, form a substituted or unsubstituted, five- or six-membered ring, $R^5$ is $(C_1-C_{10})$alkyl and $R^6$ and $R^7$ are hydrogen.

3. The process as claimed in claim 1, wherein, in the formulae IV and IVa, $R^1$, $R^2$, $R^3$ and $R^4$ are identical or different and are hydrogen or $(C_1-C_{10})$alkyl, or the radicals $R^1$ and $R^2$, $R^2$ and $R^3$ or $R^3$ and $R^4$, together with the atoms connecting them, form a substituted or unsubstituted, six-membered, saturated or unsaturated carbocyclic ring, $R^5$ is methyl, and $R^6$ and $R^7$ are hydrogen.

4. The process as claimed in claim 1, wherein the molar ratio between compound I: compound II or compound III: hydrogen fluoride is 1:0.5–2.0:5–100.

5. The process as claimed in claim 1, wherein a compound of the formula I is reacted with a compound of the formula II.

6. The process as claimed in claim 1, wherein, in said compound of formula I, at least one of $R^1$ to $R^4$ is $C_1$- to $C_{10}$-alkoxy.

* * * * *